(12) United States Patent
Xia et al.

(10) Patent No.: US 9,575,049 B2
(45) Date of Patent: Feb. 21, 2017

(54) METHOD FOR ACCURATELY TESTING YARN HAIRINESS THROUGH STRETCHING ONE-DIRECTIONALLY

(71) Applicant: Wuhan Textile University, Wuhan, Hubei (CN)

(72) Inventors: Zhigang Xia, Hubei (CN); Weilin Xu, Hubei (CN); Wenxiang Ye, Hubei (CN); Genyang Cao, Hubei (CN)

(73) Assignee: Wuhan Textile University, Wuhan, Hubei (CN)

( * ) Notice: Subject to any disclaimer, the term of this patent is extended or adjusted under 35 U.S.C. 154(b) by 29 days.

(21) Appl. No.: 14/841,709

(22) Filed: Sep. 1, 2015

(65) Prior Publication Data
US 2016/0116452 A1    Apr. 28, 2016

(30) Foreign Application Priority Data
Oct. 24, 2014   (CN) .......................... 2014 1 0576467

(51) Int. Cl.
*G01N 33/66*   (2006.01)
*G01N 33/36*   (2006.01)

(52) U.S. Cl.
CPC .................................. *G01N 33/365* (2013.01)

(58) Field of Classification Search
None
See application file for complete search history.

(56) References Cited

U.S. PATENT DOCUMENTS

| | | | | |
|---|---|---|---|---|
| 4,736,898 A * | 4/1988 | Raasch | ................. | B65H 54/34 242/475.7 |
| 4,845,983 A * | 7/1989 | Heusser | .............. | G01N 33/365 73/160 |
| 4,862,741 A * | 9/1989 | Heusser | .............. | G01N 33/365 73/159 |
| 5,393,002 A * | 2/1995 | Greis | ................... | B65H 54/346 242/118.3 |
| 5,421,529 A * | 6/1995 | Hans | .................. | B65H 63/0322 15/214 |
| 5,560,194 A * | 10/1996 | Shofner | ................ | D01H 13/32 57/264 |
| 6,332,311 B1 * | 12/2001 | Todo | .................... | B65H 54/705 242/128 |
| 2002/0023422 A1 * | 2/2002 | Stephan | ............... | B65H 51/205 57/400 |
| 2008/0209998 A1 * | 9/2008 | Schulthess | .......... | G01N 33/365 73/159 |

(Continued)

*Primary Examiner* — Andre Allen

(57) ABSTRACT

A method for accurately testing yarn hairiness through stretching one-directionally, belonging to a technical field of textile testing, is provided. A suction pipe is provided on an external side of a laser and connected with an exhausting fan through a sleeve connector and a hose. An air inlet of the suction pipe generates a negative pressure under an effect of the exhausting fan to laterally suck the yarn running at a tension state among the laser, a projection receiver and the suction pipe. The hairiness on a yarn surface stretches straight one-directionally towards an airflow direction at a height of a center of the air inlet of the suction pipe. The one-directional straight stretched hairiness on the yarn surface is accurately projected to the projection receiver of a testing head at an equal length for accurately testing a hair amount and a hair length.

12 Claims, 1 Drawing Sheet

(56) References Cited

U.S. PATENT DOCUMENTS

2013/0068010 A1\* 3/2013 Ziganek ................ G01N 33/36
  73/159
2014/0283496 A1\* 9/2014 Stahlecker ............... D01H 4/48
  57/263

\* cited by examiner

METHOD FOR ACCURATELY TESTING YARN HAIRINESS THROUGH STRETCHING ONE-DIRECTIONALLY

CROSS REFERENCE OF RELATED APPLICATION

The present invention claims priority under 35 U.S.C. 119(a-d) to CN 201410576467.0, filed Oct. 24, 2014.

BACKGROUND OF THE PRESENT INVENTION

Field of Invention

The present invention relates to a method for accurately testing yarn hairiness through stretching one-directionally, which belongs to a technical field of textile testing.

Description of Related Arts

Hairiness is one of the important indexes of the yarn quality. Yarn hairiness is the fiber tail or the fiber loop exposed on the surface of the staple yarn. When the yarn is under a stress, the hairiness lacks holding points for resisting the tensile force and thus the hairiness is unhelpful to the yarn strength. When the yarn has excessive hairs, the friction force of the yarn increases and the yarn is liable to be broken in the subsequent process, which affects the processing efficiency. During the weaving process, the excessive hairs lead to the intertwined yarn and the unclear opening of the warping yarns, lowering the weaving efficiency and the weaving quality. The yarn hairiness further affects the appearance quality of the finished product. Thus, an accurate and fast testing of the yarn hairiness is the basic requirement in the textile enterprise.

The conventional methods for testing the yarn hairiness comprise the visual observation method, the weighing method and the photoelectric method. The visual observation method is to observe the yarn hairiness with the naked eyes after being magnified by the microscope. The weighing method comprises steps of: weighing the yarn, before and after cutting or burning off the hairiness; and then obtaining the weight ratio of the hairiness. The visual observation method and the weighing method are accurate and reliable. However, the visual observation method and the weighing method cost too much time, have a low efficiency and are unable to satisfy the requirement of the large-scale rapid test of the factory. The photoelectric method comprises steps of: converting the optical signal generated by the hairiness into the electric signal; and testing the yarn hairiness rapidly. The main commercial testers for the photoelectric method comprise: Uster hairiness tester, Switzerland; G566 hairiness tester of Zweigle, Germany; SDL098/98 hairiness tester of Shieley, England; and YG172A yarn hairiness tester of Changling, China. The US patent U.S. Pat. No. 4,948,260, Method and apparatus for examining hairiness of yarn, published on Aug. 14, 1990, disclosed the Uster hairiness tester for testing the yarn hairiness through a diffuse reflection. The testing principles of the Uster hairiness tester are described as follows. A continuous monochromatic light source (laser) is shined on the prominent hairiness of the yarn body; the hairiness scatters the parallel light; the yarn body is non-transparent and dark-colored, and the prominent hairiness of the yarn body leads to a bright-colored scatted light which is detected by the optical sensor; and the hairiness value H is tested, wherein the hairiness value H is the ratio of the total length to the testing length of the hairiness, without any unit. The testing method of the G566 hairiness tester comprises a step of: counting the amount of the yarn hairs for different lengths, through twelve corresponding photosensitive diodes which are arranged at different intervals. However, the G566 hairiness tester is merely able to count the hair amount of a single side of the yarn and has a large testing deviation. Thus, the G566 hairiness tester is not common in the enterprises. The SDL098/98 hairiness tester examines the yarn hairiness through the projection counting method. The projection counting method comprises steps of: adjusting the photoelectric detecting element to the appropriate position distant from the yarn according to the pre-set testing length of the hairiness, wherein the photoelectric detecting element is the photosensitive element; passing the testing point by the yarn at a constant speed; generating a luminous flux variation, due to sweeping over the photosensitive element by the prominent hairiness which is longer than the pre-set testing length; converting the luminous flux variation into the electric signal and then generating a counting pulse; and, obtaining the hairiness index of the pre-set testing hair length, wherein the hairiness index is the total amount of the counting pulses within the pre-set testing length of the yarn. The SDL098/98 hairiness tester has the similar technical principles with the YG172A hairiness tester of China. Both the SDL098/98 hairiness tester and the YG172A hairiness tester adopt the projection counting method.

Currently, the textile enterprises mainly adopt the Uster hairiness tester and the YG172A hairiness tester. The Uster hairiness tester has following advantages of: a fast testing speed, up to 400 m/min; a large sample testing amount; an automatic test; stable testing data and a high reproducibility; no interference caused by the dirt, the yarn guiding method and the testing speed during the test. However, the Uster hairiness tester has fatal defects. The fiber colors and the spatial electromagnetic waves affect the testing results; particularly, the Uster hairiness test is unable to reflect the yarn hair amount and the hairiness distribution, and has very limited information for describing the yarn hairiness. In accordance to the fatal defects of the Uster hairiness tester, the YG172A hairiness tester is able to test the index of the yarn hairs with different lengths ranging from 1 mm to 9 mm. The YG172A hairiness tester is able to intuitionally reflect the distribution of the various yarn hairs, without being affected by the fiber colors and the spatial electromagnetic waves. Unfortunately, it is well known that the hairiness surrounds the yarn; and, the YG172A hairiness tester, through the projection counting method, merely tests the hair amount of the single side of the yarn. Particularly, when the yarn runs at a certain running speed, the running speed induces the lodging of the yarn hairiness, leading to an inaccurate testing result, a poor repeatability and a low testing speed (generally 30 m/min).

With regard to the problem that the projection counting method merely tests the hair amount of the single side of the yarn, the article titled *A new hairiness tester, cross section projection type*, written by Hiramatsu T., Shimizu T. and Kinoshita K., published on *Journal of The Textile Machinery Society of Japan,* 22(4): 108-109 (1976), disclosed a method for testing the amount of the hairiness surrounding the yarn through projecting the cross section of the yarn. However, the method has an inconvenient operation and a poor visibility, and is unable to radically improve the testing result of the yarn hairiness. The main reason lies in the key technical problems of the lodging and the bending of the hairiness on the yarn surface during running the yarn dynamically, which remain unsolved. With regard to the above key technical problems, the Chinese patent publication CN101576503A, Electrostatic yarn hairiness tester, published on Nov. 11, 2009, disclosed that: the yarn entering the testing area is applied with the high-voltage static, which induces the mutual rejection and separation among the different yarn hairiness and between the hairiness and the yarn body, thereby stretching the hairiness straight; and, the electric machine is provided parallel with the yarn for attracting the hairiness, in such a manner that the yarn hairiness is almost vertical to the yarn body. According to the experiments, the electrostatic yarn hairiness tester has a good effect for the static yarn within a short time, but fails to vertically stretch the hairiness on the surface of the yarn which runs at a high speed. Particularly, because the yarn hairiness stretches along the different radial directions of the yarn body and stretches vertically to the yarn body, the hairiness of the different radial directions is unable to be all accurately projected to the projection receiver of the testing head at an equal length (i. e., the hair projection cannot be accurately equal to the hair true configuration for the most yarn hairs). Moreover, the high-voltage static causes the potential safety risk. The fiber static seriously attenuates to reduce the radial hair-stretching force in the air with certain humidity. Therefore, the electrostatic yarn hairiness tester fails in the industrial application. With regard to the key technical problems of the lodging and the bending of the hairiness on the yarn surface during running the yarn dynamically, the Chinese patent publication CN101671946A, Device for testing hairiness state of yarn under high-speed airflow, published on Mar. 17, 2010, disclosed a hairiness testing device which releases the high-pressure airflow to the hairiness surrounding the yarn which runs at the high speed, through the annular airflow channel. According to the aerodynamics, the flowing speed is different due to the different distances from the annular airflow outlet; the hairiness of different lengths has different air resistances. Thus, through the hairiness testing device, the hairiness on the surface of the yarn which runs at the high speed fails to fully stretch to be vertical to the yarn body. Similar to the electrostatic yarn hairiness tester, the hairiness testing device has the hairiness stretching in the different radial directions of the yarn body and vertically to the yarn body. The hairiness of the different radial directions is still unable to project the entire hairs' true configurations accurately on the projection receiver of the testing head for an accurately testing. Thus, the above methods and the devices all fail to solve the problem that the projection counting method is unable to rapidly, effectively, accurately and stably test the yarn hairiness.

SUMMARY OF THE PRESENT INVENTION

An object of the present invention is to overcome the above problems and provide a method for accurately testing yarn hairiness through stretching one-directionally, so as to effectively stretch the hairiness on a yarn surface and accurately test a hair length and a hair amount on the yarn surface. In order to accomplish the above object, the present invention adopts the following technical solutions.

A method for accurately testing yarn hairiness through stretching one-directionally comprises steps of:
  unwinding off a yarn from a bobbin yarn package which is provided on a supporter;
  passing the yarn successively through a tension yarn guiding device, a brushing wheel, a first yarn guiding wheel and a second yarn guiding wheel which are provided on a pre-operation platform of a hairiness tester;
  entering a hairiness testing area by the yarn, wherein the hairiness testing area comprises a testing head, a laser, a third yarn guiding wheel and a fourth yarn guiding wheel, wherein: the laser is provided between the third yarn guiding wheel and the fourth yarn guiding wheel; and a projection receiver of the testing head corresponds to the laser;
  passing the yarn which enters the hairiness testing area through the third yarn guiding wheel, and then passing the yarn, at a tension state, through a central position between the laser and the projection receiver;
  moving the yarn out of the hairiness testing area via the fourth yarn guiding wheel;
  after moving out of the hairiness testing area, passing the yarn successively through a fifth yarn guiding wheel and a fixed yarn guiding groove;
  pulling the yarn by a driving roller and a driven roller; and finally, falling into a waste yarn collecting container;
  wherein: a suction pipe is provided on an external side of the laser; the suction pipe is provided between the laser and the projection receiver of the testing head; an end plane of an air inlet of the suction pipe is rectangle; the rectangle end plane of the air inlet has a width of 3-30 mm; a length of the rectangle end plane of the air inlet is larger than or equal to a diameter of the laser; a center of the end plane of the air inlet of the suction pipe and a center of the laser are located at the same horizontal plane; the end plane of the air inlet of the suction pipe is vertical to a plane of the laser and tangent to an edge line of an emitting surface of the laser; the end plane of the air inlet of the suction pipe is parallel with the yarn running between the laser and the projection receiver; the suction pipe is fixed on the pre-operation platform of the hairiness tester through a sleeve connector; the sleeve connector is connected with an exhausting fan through a hose; the air inlet of the suction pipe generates a negative pressure under an effect of the exhausting fan, so as to laterally suck the yarn running at the tension state among the laser, the projection receiver and the air inlet of the suction pipe; all the hairiness on a yarn surface in the hairiness testing area stretches straight towards an airflow direction, at a height of a center of the air inlet of the suction pipe; and then, the one-directional straight stretched hairiness on the yarn surface is accurately projected to the projection receiver of the testing head at an equal length, so as to accurately test a hair amount and a hair length.

The negative pressure generated by the air inlet of the suction pipe is at a range of 50-5000 Pa.

Compared with the conventional hairiness testing method, the method for accurately testing the yarn hairiness through stretching one-directionally, provided by the present invention, has following advantages. The suction pipe is provided on the external side of the laser; the suction pipe is connected with the exhausting fan through the sleeve connector and the hose; the air inlet of the suction pipe generates the negative pressure under the effect of the exhausting fan, so as to laterally suck the yarn running at the tension state among the laser, the projection receiver and the air inlet of the suction pipe; the hairiness on the yarn surface stretches straight one-directionally towards the airflow direction, at the height of the center of the air inlet of the suction pipe; and, the one-directional straight stretched hairiness on the yarn surface is accurately projected to the projection receiver of the testing head at the equal length, so as to accurately test the hair amount and the hair length. Therefore, the following technical problems are solved by the present invention: the conventional hairiness testers are unable to accurately project the hairiness sticking to the yarn surface; a static method and an annular airflow channel blowing method merely stretch the yarn hairiness along different radial directions vertically to a yarn body; the static method and the annular airflow channel blowing method are unable to accurately project all the straight stretched yarn hairiness to the projection receiver of the testing head at the equal length. According to the present invention, the hairiness on the yarn surface is sucked one-directionally by the airflow, so as to avoid a danger of high-voltage static fire. The testing yarn of the present invention has a wide variety. The smaller negative pressure generated by the air inlet of the suction pipe, the larger suction airflow strength, so as to satisfy an accurate test of the hairiness having different rigidity on the yarn surface. The negative pressure suction device of the hairiness tester for accurately testing the yarn hairiness through stretching one-directionally has a simple structure and a convenient operation, and is applicable in wide promotion.

These and other objectives, features, and advantages of the present invention will become apparent from the following detailed description, the accompanying drawings, and the appended claims.

DETAILED DESCRIPTION OF THE PREFERRED EMBODIMENT

Figure 1:
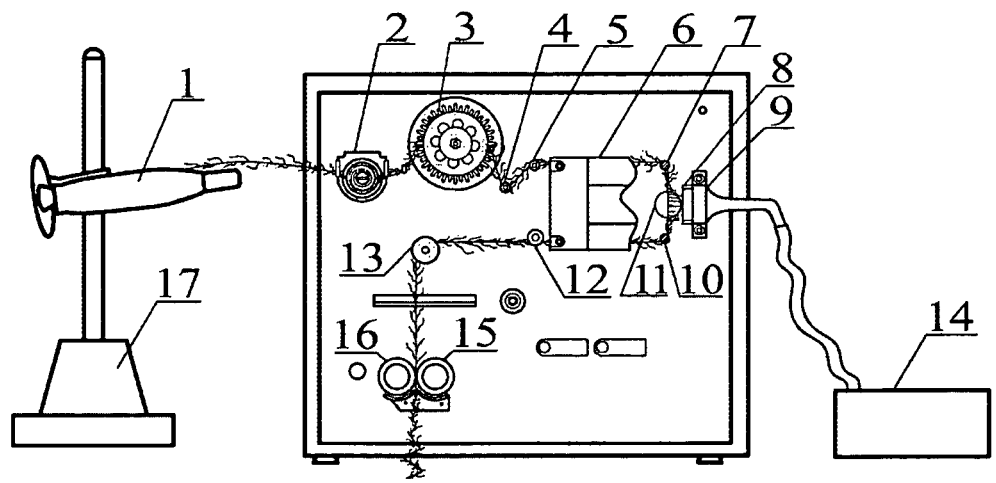
FIG. 1 is a sketch view of a method for accurately testing yarn hairiness through stretching one-directionally according to a preferred embodiment of the present invention.

Referring to the drawings, a method for accurately testing yarn hairiness through stretching one-directionally, provided by the present invention, is further illustrated.

Figure 2:
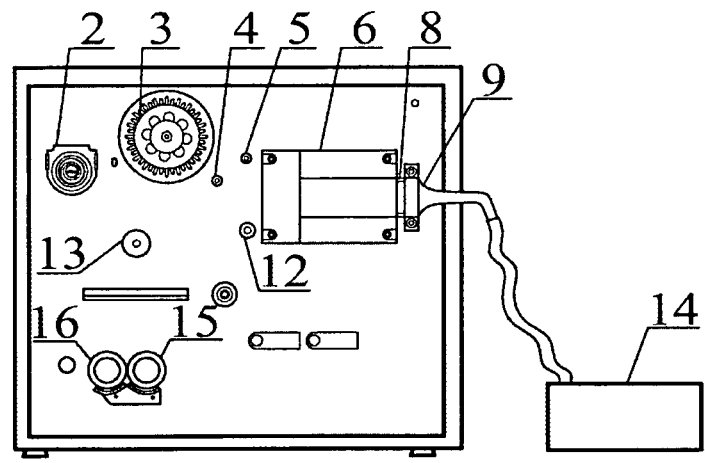
FIG. 2 is a structural diagram of a hairiness tester for accurately testing the yarn hairiness through stretching one-directionally according to the preferred embodiment of the present invention.

As showed in FIG. 1 and FIG. 2, the method for accurately testing the yarn hairiness through stretching one-directionally comprises steps of:
  unwinding off a yarn from a bobbin yarn package 1 which is provided on a supporter 17;
  passing the yarn successively through a tension yarn guiding device 2, a brushing wheel 3, a first yarn guiding wheel 4 and a second yarn guiding wheel 5 which are provided on a pre-operation platform of a hairiness tester;
  entering a hairiness testing area by the yarn, wherein the hairiness testing area comprises a testing head 6, a laser 11, a third yarn guiding wheel 7 and a fourth yarn guiding wheel 10, wherein: the laser 11 is provided between the third yarn guiding wheel 7 and the fourth yarn guiding wheel 10; a projection receiver of the testing head 6 corresponds to the laser 11; and the third yarn guiding wheel 7 and the fourth yarn guiding wheel 10 are provided on the testing head 6;
  passing the yarn which enters the hairiness testing area through the third yarn guiding wheel 7, and then passing the yarn, at a tension state, through a central position between the laser 11 and the projection receiver;
  providing a suction pipe 8 on an external side of the laser 11, wherein: the suction pipe 8 is provided between the laser 11 and the projection receiver of the testing head 6; an end plane of an air inlet of the suction pipe 8 is rectangle; the rectangle end plane of the air inlet has a width of 3-30 mm; a length of the rectangle end plane of the air inlet is larger than or equal to a diameter of the laser 11; a length direction of the rectangle air inlet is consistent with a running direction of the yarn; a center of the end plane of the air inlet of the suction pipe 8 and a center of the laser 11 are located at the same horizontal plane; the end plane of the air inlet of the suction pipe 8 is vertical to a plane of the laser 11 and tangent to an edge line of an emitting surface of the laser 11; the end plane of the air inlet of the suction pipe 8 is parallel with the yarn running between the laser 11 and the projection receiver, in such a manner that the yarn running between the laser 11 and the projection receiver is fully sucked by a negative pressure which is generated by the air inlet of the suction pipe 8; an air outlet of the suction pipe 8 is tightly fixed with a first end of a sleeve connector 9; the sleeve connector 9 is fixed on the pre-operation platform of the hairiness tester through screws; the suction pipe 8 is fixed on the pre-operation platform of the hairiness tester through the sleeve connector 9; and a second end of the sleeve connector 9 is connected with an exhausting fan 14 through a hose;
  generating an airflow by the air inlet of the suction pipe 8 under an effect of the exhausting fan 14, wherein the negative pressure generated by the suction pipe 8 at the air inlet is at a range of 50-5000 Pa; if the hairiness on a yarn surface has a large rigidity or a large resilience, such as ramie and wool yarn, a strong suction airflow is required at the air inlet of the suction pipe 8 and the negative pressure generated by the air inlet of the suction pipe 8 is required to be small (50-500 Pa) to stretch the hairiness on the yarn surface straight in one-direction; and, if the hairiness on the yarn surface has a small rigidity, such as cotton yarn, merely a weak suction airflow is required at the air inlet of the suction pipe and the negative pressure generated by the air inlet of the suction pipe 8 is required to be large (500-5000 Pa) to stretch the hairiness on the yarn surface straight in one-direction;
  laterally sucking the yarn running at the tension state among the laser 11, the projection receiver and the suction pipe 8, by the airflow, so as to stretch all the hairiness on the yarn surface in the hairiness testing area straight one-directionally towards an airflow direction at a height of the center of the air inlet of the suction pipe 8;
  accurately projecting the one-directional straight stretched hairiness on the yarn surface to the projection receiver of the testing head at an equal length, so as to accurately test a hair amount and a hair length;
  moving the tested yarn out of the hairiness testing area via the fourth yarn guiding wheel 10;
  after moving out of the hairiness testing area, passing the yarn successively through a fifth yarn guiding wheel 12 and a fixed yarn guiding groove 13;
  entering a roller nip by the yarn, wherein the roller nip is formed by a driving roller 15 and a driven roller 16;
  pulling the yarn by the driving roller 15 and the driven roller 16; and
  finally, falling into a waste yarn collecting container.

One skilled in the art will understand that the embodiment of the present invention as shown in the drawings and described above is exemplary only and not intended to be limiting.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A method for accurately testing yarn hairiness through stretching one-directionally, comprising steps of:
   unwinding off a yarn from a bobbin yarn package which is provided on a supporter;
   passing the yarn successively through a tension yarn guiding device, a brushing wheel, a first yarn guiding wheel and a second yarn guiding wheel which are provided on a pre-operation platform of a hairiness tester;
   entering a hairiness testing area by the yarn, wherein the hairiness testing area comprises a testing head, a laser, a third yarn guiding wheel and a fourth yarn guiding wheel, wherein: the laser is provided between the third yarn guiding wheel and the fourth yarn guiding wheel; and a projection receiver of the testing head corresponds to the laser;
   passing the yarn which enters the hairiness testing area through the third yarn guiding wheel, and then passing the yarn, at a tension state, through a central position between the laser and the projection receiver;
   moving the yarn out of the hairiness testing area via the fourth yarn guiding wheel;
   after moving out of the hairiness testing area, passing the yarn successively through a fifth yarn guiding wheel and a fixed yarn guiding groove;
   pulling the yarn by a driving roller and a driven roller; and finally, falling into a waste yarn collecting container;
   wherein: a suction pipe is provided on an external side of the laser; the suction pipe is provided between the laser and the projection receiver of the testing head; an end plane of an air inlet of the suction pipe is rectangle; the rectangle end plane of the air inlet has a width of 3-30 mm; a length of the rectangle end plane of the air inlet is larger than or equal to a diameter of the laser; a center of the end plane of the air inlet of the suction pipe and a center of the laser are located at the same horizontal plane; the end plane of the air inlet of the suction pipe is vertical to a plane of the laser and tangent to an edge line of an emitting surface of the laser; the end plane of the air inlet of the suction pipe is parallel with the yarn running between the laser and the projection receiver; the suction pipe is fixed on the pre-operation platform of the hairiness tester through a sleeve connector; the sleeve connector is connected with an exhausting fan through a hose; the air inlet of the suction pipe generates a negative pressure under an effect of the exhausting fan, so as to laterally suck the yarn running at the tension state among the laser, the projection receiver and the suction pipe; all the hairiness on a yarn surface in the hairiness testing area stretches straight one-directionally towards an airflow direction, at a height of a center of the air inlet of the suction pipe; and, the one-directional straight stretched hairiness on the yarn surface is accurately projected to the projection receiver of the testing head at an equal length, so as to accurately test a hair amount and a hair length.

2. The method for accurately testing the yarn hairiness through stretching one-directionally, as recited in claim 1, wherein the negative pressure generated by the air inlet of the suction pipe is at a range of 50-5000 Pa.

3. The method for accurately testing the yarn hairiness through stretching one-directionally, as recited in claim 1, wherein a length direction of the rectangle air inlet is consistent with a running direction of the yarn.

4. The method for accurately testing the yarn hairiness through stretching one-directionally, as recited in claim 1, wherein: an air outlet of the suction pipe is tightly fixed with a first end of the sleeve connector; the exhausting fan is connected with a second end of the sleeve connector through the hose; and, the sleeve connector is fixed on the pre-operation platform of the hairiness tester through screws.

5. The method for accurately testing the yarn hairiness through stretching one-directionally, as recited in claim 2, wherein: when the hairiness on the yarn surface has a large rigidity or a large resilience, a strong suction airflow is required at the air inlet of the suction pipe and the negative pressure generated by the air inlet of the suction pipe is required to be 50-500 Pa, to stretch the hairiness on the yarn surface straight in one direction.

6. The method for accurately testing the yarn hairiness through stretching one-directionally, as recited in claim 2, wherein: when the hairiness on the yarn surface has a small rigidity, merely a weak suction airflow is required at the inlet of the suction pipe and the negative pressure generated by the air inlet of the suction pipe is required to be 500-5000 Pa, to stretch the hairiness on the yarn surface straight in one direction.

7. A hairiness tester for accurately testing yarn hairiness through stretching one-directionally, comprising:
   a tension yarn guiding device, a brushing wheel, a first yarn guiding wheel and a second yarn guide wheel which are provided on a pre-operation platform of said hairiness tester, wherein a yarn successively passes through said tension yarn guiding device, said brushing wheel, said first yarn guiding wheel and said second yarn guiding wheel and then enters a hairiness testing area;
   a testing head, a laser, a third yarn guiding wheel and a fourth yarn guiding wheel which are located at said hairiness testing area, wherein: said laser is provided between said third yarn guiding wheel and said fourth yarn guiding wheel; said testing head comprises a projection receiver which corresponds to said laser; said third yarn guiding wheel and said fourth yarn guiding wheel are provided on said testing head, in such a manner that the yarn which enters said hairiness testing area passes through said third yarn guiding wheel and then, at a tension state, passes through a central position between said laser and said projection receiver;
   a suction pipe which is provided on an external side of said laser and between said laser and said projection receiver of said testing head, wherein: an end plane of an air inlet of said suction pipe is rectangle; said rectangle end plane of said air inlet has a width of 3-30 mm; a length of said rectangle end plane of said air inlet is larger than or equal to a diameter of said laser; a center of said end plane of said air inlet of said suction pipe and a center of said laser are located at a same horizontal plane; said end plane of said air inlet of said suction pipe is vertical to a plane of said laser and tangent to an edge line of an emitting surface of said laser; and, said end plane of said air inlet of said suction pipe is parallel with the yarn running between said laser and said projection receiver, in such a manner that the yarn running between said laser and said projection receiver is fully sucked by a negative pressure which is generated by said air inlet of said suction pipe;

a sleeve connector for fixing said suction pipe on said pre-operation platform of said hairiness tester;

an exhausting fan connected with said sleeve connector through a hose, wherein: said air inlet of said suction pipe generates said negative pressure under an effect of said exhausting fan; said negative pressure laterally sucks the yarn running at the tension state among said laser, said projection receiver and said air inlet of said suction pipe; the hairiness on a yarn surface stretches straight towards an airflow direction, at a height of a center of said air inlet of said suction pipe; the one-directional straight stretched hairiness on the yarn surface is accurately projected to said projection receiver of said testing head at an equal length, so as to accurately test a hair amount and a hair length; and said fourth yarn guiding wheel is for moving the tested yarn out of said hairiness testing area; and a fifth yarn guiding wheel, a fixed yarn guiding groove, a roller nip comprising a driving roller and a driven roller and a waste yarn collecting container, wherein the yarn which moves out of said hairiness testing area enters said roller nip through said fifth yarn guiding wheel and said fixed yarn guiding groove; the yarn is pulled by said driving roller and said driven roller and then falls into said waste yarn collecting container.

8. The hairiness tester, as recited in claim 7, wherein said negative pressure generated by said air inlet of said suction pipe is at a range of 50-5000 Pa.

9. The hairiness tester, as recited in claim 7, wherein a length direction of said rectangle air inlet is consistent with a running direction of the yarn.

10. The hairiness tester, as recited in claim 7, wherein: an air outlet of said suction pipe is tightly fixed with a first end of said sleeve connector; said exhausting fan is connected with a second end of said sleeve connector through said hose; and, said sleeve connector is fixed on said pre-operation platform of said hairiness tester through screws.

11. The hairiness tester, as recited in claim 8, wherein: when the hairiness on the yarn surface has a large rigidity or a large resilience, a strong suction airflow is required at said air inlet of said suction pipe and said negative pressure generated by said air inlet of said suction pipe is required to be 50-500 Pa, to stretch the hairiness on the yarn surface straight.

12. The hairiness, tester, as recited in claim 8, wherein: when the hairiness on the yarn surface has a small rigidity, merely a weak suction airflow is required at said air inlet of said suction pipe and said negative pressure generated by said air inlet of said suction pipe is required to be 500-5000 Pa, to stretch the hairiness on the yarn surface straight.

* * * * *